United States Patent [19]

Meinke et al.

[11] 4,114,623

[45] Sep. 19, 1978

[54] CUTTING AND COAGULATION APPARATUS FOR SURGERY

[75] Inventors: Hans Heinrich Meinke, Gauting; Gerhard Flachenecker, Ottobrunn; Karl Fastenmeier; Friedrich Landstorfer, both of Munich; Heinz Lindenmeier, Planegg, all of Fed. Rep. of Germany

[73] Assignee: Karl Storz Endoscopy-America, Inc., Los Angeles, Calif.

[21] Appl. No.: 709,610

[22] Filed: Jul. 29, 1976

[51] Int. Cl.$^2$ ............... A61B 17/36; A61N 3/02
[52] U.S. Cl. ...................... 128/303.14; 128/303.17
[58] Field of Search .............. 128/303.13, 303.14, 128/303.17, 303.18, 2.1 P

[56] References Cited

U.S. PATENT DOCUMENTS

| 3,163,165 | 12/1964 | Isikawa | 128/303.17 |
| 3,601,126 | 8/1971 | Estes | 128/303.14 |
| 3,675,655 | 7/1972 | Sittner | 128/303.14 |
| 3,875,945 | 4/1975 | Friedman | 128/303.14 |
| 3,963,030 | 6/1976 | Newton | 128/303.17 |
| 4,024,467 | 5/1977 | Andrews et al. | 128/303.14 X |

FOREIGN PATENT DOCUMENTS

| 1,209,247 | 2/1960 | France | 128/303.17 |
| 1,347,865 | 11/1963 | France | 128/303.14 |

Primary Examiner—Robert W. Michell
Assistant Examiner—Lee S. Cohen
Attorney, Agent, or Firm—Donald D. Mon

[57] ABSTRACT

A device and system for the cutting and/or coagulation of human tissue with the use of high frequency currents. This invention is used to cut materials similar to the human tissue which can emit steam or gassy products when sufficiently heated. It controls the extent of the arc generated during the cutting operation, and controls the heat generated during the coagulating operation, both of these for the purpose of minimizing formation of harmful forms of albumen.

17 Claims, 5 Drawing Figures

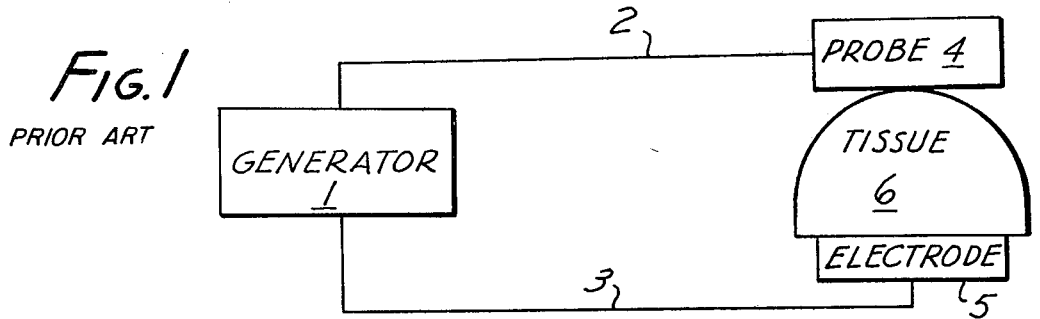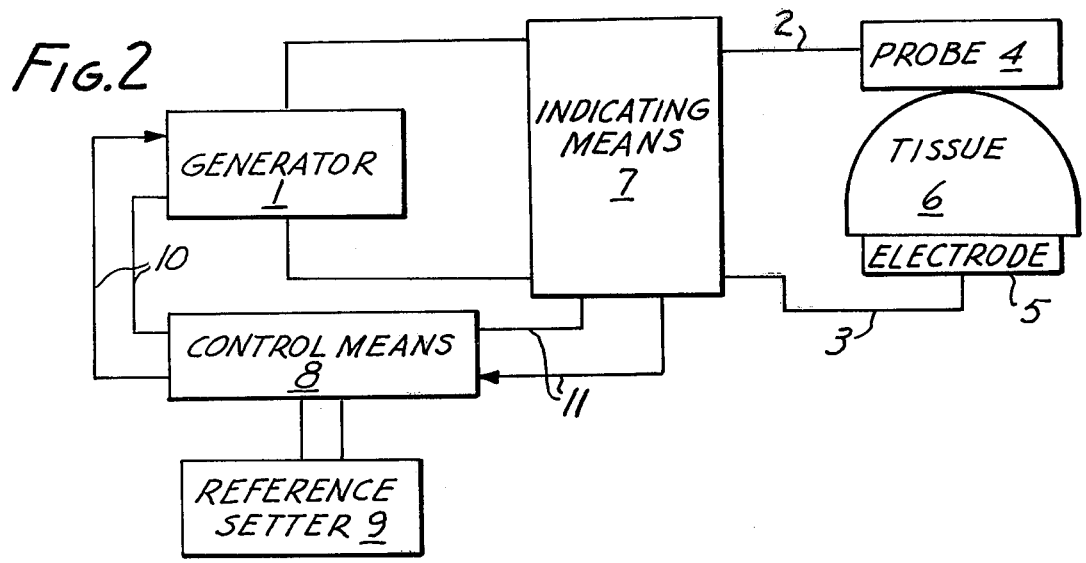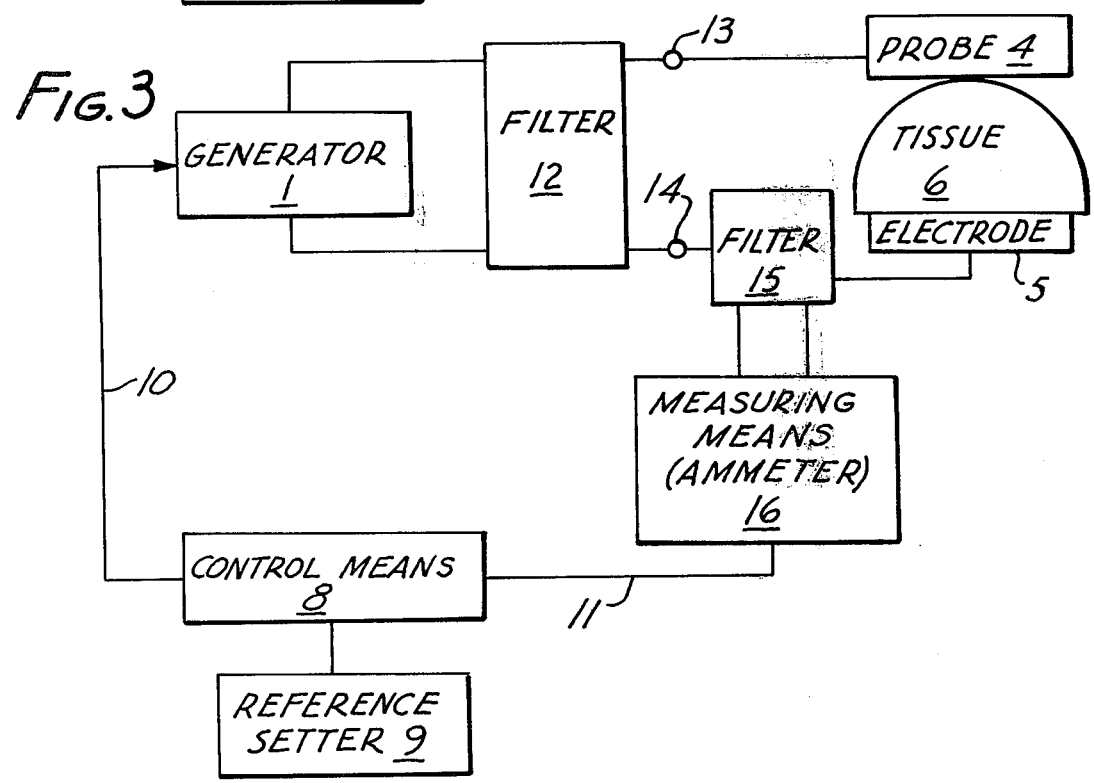

CUTTING AND COAGULATION APPARATUS FOR SURGERY

This invention relates to a device for the cutting and/or coagulation of human tissue with the use of high frequency currents. This invention is generally useful for the surgical cutting of materials that are similar to human tissue; that is, such materials as will emit steam or gassy products when sufficiently heated, and which have enough conductivity of dielectric losses that they will be heated by high frequency currents.

It is a well-established procedure to cut human tissue with the use of a probe in the form of a thin wire or a thin knife, using a high frequency alternating electrical current applied to the tissue by the probe acting as one electrode. The other electrode is attached elsewhere to the body. The thin probe has a small cross-section where it touches the area of the body to be cut, and therefore there is a very high current density at this place. The term "probe" includes a knife, a thin wire, or any other suitably thin current-applying body. Because of the relatively large resistance loss in the human tissue with the use of high frequency currents, there occurs a heating of the tissue, especially in view of the high current density at the small-area point of contact of the probe with the tissue. Because the tissue contains water or fat (substances that will steam away), the alternating current creates a steaming off of fluid in the tissue, thereby destroying the cell walls. This will occur at higher temperatures in the proximal areas of the point of contact of the probe and will cause a division of the tissue at this region. Pushing the probe along will cause a continuous cut to be made in this manner.

It is well known that, by means of the aforementioned procedure, a bloodless cut can be made. This derives from the fact that heating of the cut tissue causes a boiling of the albumen and sealing of the capillaries. If larger blood vessels are cut, the usual procedure for sealing the vessel is to halt the probe for a time at the respective area in order to provide a greater amount of heat, and spread this heat to and through the tissue, the wall of the artery, and the blood, for the purpose of causing coagulation.

At the moment when the steaming away of water or fat occurs, the immediate region of contact between the probe and the tissue changes into a gaseous separation layer. The high frequency current flows through this gaseous separation layer with the help of an electric arc that itself produces a very high temperature. This high temperature may lead to the destruction of albumen to a larger extent than is desirable, and especially may lead to the production of poisonous forms of albumen. The poisonous forms of albumen will seriously hinder the healing process which follows the surgery and are therefore undesirable. Furthermore, the electric arc produces a mixture of gaseous oxygen and hydrogen from the water. The high frequency current used for cutting the tissue has been known to cause dangerous oxygen-hydrogen explosions. Accordingly, it is desirable to control the existence and effects of the electric arc.

The adjustment of the high frequency current to the correct intensity is critical since, on the one hand, cutting will only occur as the consequence of formation of gases, but on the other hand, an excessive electric arc has to be avoided because of the damage it might do, for example, excessive formation of deleterious forms of albumen. However, for the rapid sealing of the larger vessels, sufficient heat should be made available, but without the presence of an electric arc.

To complicate matters further, human tissue is not homogenous, and an incision may progress through zones of different types of tissue, for example, through regions of greater water density, through scar tissue of little water density, through fat, and through skin. So the electrical resistance of the tissue will usually vary with the progress of the incision, as will the current passed through the circuit, and the formation of gases. For this reason, if an unregulated generator is used, sometimes too much gas formation and too strong an electric arc will occur, while at other times not enough heat will be available and the cutting process will stop. Therefore, during the cutting process, the magnitude of the high frequency current should be kept adjusted so as to conform to the needs of the tissue being cut at the moment. Experience shows that the usual adjustment of the current by the surgeon when using presently-known devices is hardly optimal.

It is an objective of this invention to regulate the magnitude of the high frequency current supplied to the probe, by means of an automatic control unit with a sufficiently rapid response that the current supplied at least closely conforms to the required optimal current for the tissue then being cut. This means there should always be enough current for the cutting and coagulation process, but on the other hand, only such an amount as limits the formation of electric arcs to the correct extent.

This objective finds its solution in this invention by utilizing indicating means which supply information, continuously or at predetermined intervals, about the on-going cutting and coagulation processes in the form of one or more electrical signals. There may also be provided a control means which compares the output of the indicating means to a set-point program, to produce a control voltage from the comparison. With the use of this control voltage, the output current of a high frequency generator that supplies current to the probe is adjusted to values prescribed by the set-points and suitable to the needs of the procedure at the moment.

The indicating means can be of various known types. For example, the electric arc can be sensed by optical means, and the electrical signal can be derived therefrom by the use of an optical-electrical transducer responsive to the optical means. However, all-electrical measuring methods seem to be preferable. For example, those that observe the electrical resistance of the high frequency current, or that will observe delivered power of the high frequency current to the coagulating process, are useful.

This invention will be fully understood from the following detailed description and the accompanying drawings, in which:

FIG. 1 is a schematic circuit drawing showing circuitry according to the prior art;

FIG. 2 is a schematic circuit drawing showing a simple embodiment of the invention;

FIGS. 3 and 4 are schematic circuit drawings showing two more-sophisticated embodiments of the invention.

Figure 4:
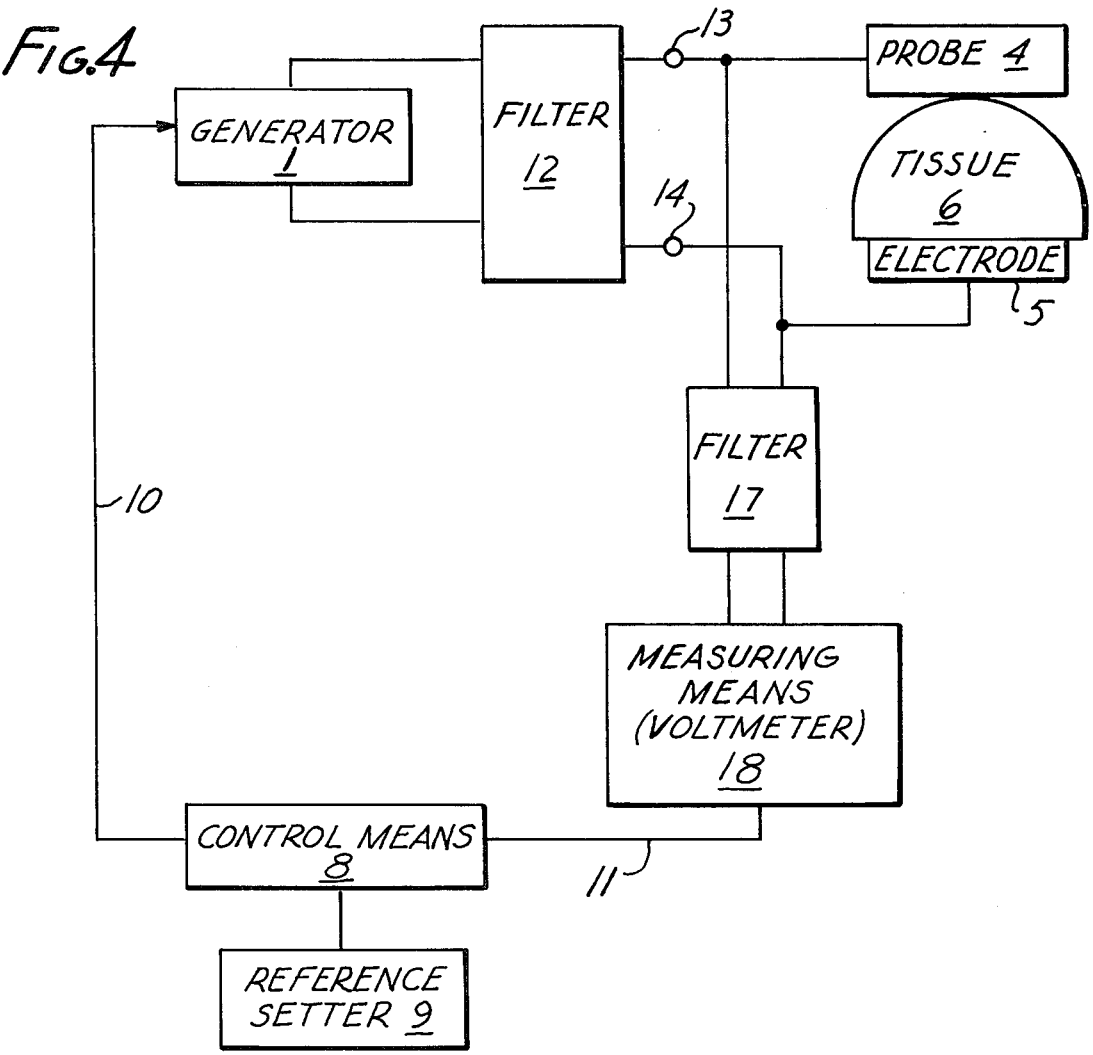

FIG. 1 shows the conventional high frequency tissue cutting device. It includes a high frequency generator 1 which produces voltage and current at high frequencies to leads 2 and 3. Lead 2 is connected to conductive probe 4 having a fine edge which will make a small-area contact with tissues 6. Probe 4 is one electrode for the system. The other electrode 5 is applied to the tissue by means of a firm wide area abutment contact. The circuit is completed through tissue 6.

Throughout the specification identical numbers are applied to identical means.

FIG. 2 shows a simple example of apparatus which will observe the cutting and/or coagulation states directly through leads 2 and 3. Indicating means 7 is connected into leads 2 and 3. The output of the indicating means is provided by means of an electrical signal to control means 8 through leads 11. This control means also receives data from a set-point program contained in a reference setter 9. Through leads 10, the magnitude of the high frequency current produced by the generator 1 is controlled as a consequence of the signal from means 8. The set-point program is selected prior to the operation by the surgeon in accordance with the procedure to be undertaken and will be more fully described below. Suffice it to say that the purpose of the control means is to determine the magnitude of the current produced by the generator, which of course has a substantial effect upon the existence and volume of an arc and the amount of heat generated.

The indicating means can respond to one or more physical values. The indicating means must measure and show the presence and strength of the electric arc, because the limitation of the volume of the electric arc to special safe values is a feature of this invention and secures an optimal medical result. On the other hand, cutting with a useful cutting speed will produce substantial amounts of gases, and the existence of a minor electric arc is inevitable. With low current magnitudes, no electric arc will start. The high frequency voltage between probe and tissue is then insufficient, and cutting does not occur. With an increase in the magnitude of the high frequency current, the electrical arc starts suddenly, when at higher currents the output voltage of the high frequency generator exceeds the ignition voltage of the electric arc. This is called the ignition point of the electric arc. The ignition point depends importantly on the characteristics of the tissue at the point of contact with the probe. The ignition point may be exceeded only slightly, if burning of albumen is to be avoided or minimized.

This invention always refers the set-point to the ignition point of the electric arc. By way of example, during a constant speed of incision, and without need for pausing for coagulation, the set-point program of the device will be arranged to control the output power of the high frequency generator in such a way that the ignition point is exceeded only slightly, and therefore a minor electric arc exists. This is also true for heterogenous tissue, because the output power of the high frequency generator will permanently be referred to the ignition point as it exists from point to point along the cutting path. In the event the coagulation procedures becomes necessary, use is made of a coagulation set-point which causes temporary changes of the current magnitude. The maximum value of the magnitude of the high frequency current is related to the ignition point of the electric arc, but arc ignition is not permitted to occur for substantial periods of time during coagulation.

From the foregoing it follows that a very precise indicating procedure for the ignition point and the strength of the electric arc is needed if the incision and coagulation procedures are to work at an optimum level. An advantageous indicating means 7 for a very accurate measurement of the ignition point, and the strength of the electric arc, will now be described. The alternating voltage produced by the generator 1 drives the current from the probe 4 into the tissue 6. At times when the instantaneous value of the high frequency voltage is small, no electric arc will exist. An electric arc will appear as the voltage increases (provided the maximum value is sufficiently high). When the voltage decreases after passing its maximum, the electric arc disappears again. Therefore, the electric arc burns, if it burns at all, only during a part of the period of the current alternation. During this time, it changes the resistance of the circuit, and influences the corresponding characteristics of the current. It is therefore possible to measure the electric arc either from the changing circuit resistance, or from the changing current, or from the changing voltage, all caused by the electric arc.

A preferred technique to make the necessary measurement is to employ the change in the current through the electric arc. As soon as the electric arc burns, the sinusoidal current delivered from the high frequency generator will be distorted by the additional "harmonic" components of the current generated from the electric arc itself. Since the distortion in the positive and the negative half-periods of the current are about equal, the distortion appears almost only as harmonic frequencies which are odd numbered (preferably tripled) relative to the working frequency from generator 1. The extent of the distortion increases with the increasing size (volume) of the electric arc. The measurement of the harmonic distortion contained within the high frequency alternating current provides an indication of the volume of the electric arc, and is well suited for control purposes in this invention.

Because the cutting procedure must work with a very small electric arc, it is important to be able to make measurements of very small harmonic current components from the arc itself. A small electric arc produces only a small amount of harmonic distortion which is of the same order of magnitude as would, without precautions, be delivered by a conventional generator 1. Therefore, a filter 12 (FIG. 3) is an important component. This filter is designed in such a way that it will pass the current of the working (base) frequency from the generator almost without attenuation. However, it attenuates and filters out currents of harmonic frequencies almost completely, and therefore prevents the power supply from delivering its usually-existing harmonic current components to the probe. Then the electric arc between probe 4 and tissues 6 is substantially the only source of harmonic current components. Measurement of these harmonics thereby provides an indication of the volume and intensity of the electric arc.

Because relatively large currents at the working frequency flow from filter 12 to probe 4 and electrode 5, in addition to the harmonic current components of the electric arc which are to be measured, another filter 15 is preferably, but not necessarily, inserted into the circuit (FIG. 3). It isolates measuring means 16 from the currents of working frequency, and passes to measuring means 16 only the harmonic current components which are to be measured.

The harmonic current components passed by filter 15 can be measured by known high frequency ammeters as one example of measuring means 16. When using a measuring means of this type, it is an advantage to design the coupling 13, 14 of the circuit to filter 12 with a very low impedance for the harmonic frequencies. Then the circuit has the lowest possible resistance to the harmonic current components, and the electric arc will produce the largest possible harmonic components. Thus, the output of the harmonics used to provide measurement is optimized.

Using modern instrumentation, it is somewhat easier to utilize the inertia-free techniques attainable with voltage measurements than indication means relying on current flow which involve elements that do possess inertia. Therefore, filter 12, in the presently preferred embodiment and best known mode for the invention, as shown in FIG. 4, is designed in such a way that the couplings 13, 14 possess a high impedance for the harmonic frequencies that are to be measured, and they are directed toward these couplings. Then the harmonic current components between couplings 13 and 14 produced by the electric arc cause correspondingly high harmonic voltage components. In FIG. 4 these components pass through filter 17 that passes them to a high frequency voltage meter 18. This is an inertia-free device. Filter 17 filters out the voltages of the basic frequency from the generator, and prevents their reaching the measuring means 18.

If the frequency of the generator is exactly defined and stable, then filter 15 (in FIG. 3) or filter 17 (in FIG. 4) can have a small band-pass, and allow essentially only one harmonic frequency (preferably the third) to pass through. If the frequency of generator 1 is not precisely defined and stable, then filters with larger band widths will be used.

In the preferred embodiment of the invention, one would use a filter with a high pass character that allows passage of all the harmonic components from the arc. This way the voltage of the harmonics to be measured will be larger and easier to measure through summing up. However, the selection of the working frequency (i.e., the frequency of the generator) may be worse than with the narrow band filter.

In order to be able to measure the ignition point of the electric arc certainly and exactly, one uses a voltage measuring device that will be sensitive enough to measure even very small voltages. In a preferred embodiment of this invention, the voltage measuring means may comprise a linear diode rectifier with a preamplifier. The band width of the preamplifier is adjusted to the frequency band of the anticipated harmonic components which are to be measured. In one beneficial arrangement, the set-point program can be adjusted by the surgeon. This regulation, in its simplest form, occurs in such a way that the signal voltage fed through line 11 (FIG. 4) is maintained at a constant level by means of the control device. Such an arrangement enables cutting with a substantially constant cutting speed, nearly independently of the tissue composition at the moment, because the high frequency current is always regulated so that a minor electric arc burns to a nearly constant extent. As long as no fairly large blood vessels have to be cut, the heating of the tissue through this "set-point" voltage program can be adjusted automatically. Then coagulation and blood volume of the tissue can be taken into account during cutting.

If the tissue has a tendency to bleed, and if not enough coagulation results along with the normal cutting process, then the set-point program will be shaped in such a way that cutting intervals and coagulating intervals will alternate, with adjustable respective pulse durations. During the cutting intervals, the control will follow the set-points of the electric arc as mentioned above. During the coagulation intervals, the magnitude of the high frequency current will be reduced from the higher values where an arc exists and cuts, to a lower level where the arc does not exist, and therefore cutting does not occur. During the coagulation intervals, the probe will be held motionless in the same place with respect to the tissue, with heating current applied at levels below those which cause an arc. This effect will heat the tissue in the contacted area to the higer temperatures which are needed so that coagulation can occur, but not to the higher temperatures which would cause steaming off and cutting.

The effect of the high frequency current depends on how much the magnitude of the current fluctuates at or below the level at which the arc will start. If a surgeon should cut an area of tissue with different characteristics from other tissue, the current magnitude has to change accordingly, because the ignition point of the electric arc also fluctuates. Therefore, the demand for current for the cutting and for the coagulation processes vary. In an advantageous form of this invention, the current magnitude of the set-point program will not be given as a constant value for all conditions and tissues, but instead is given as a relative value, relative to the reignition point of the electric arc in the tissue where the probe is working.

There are differences in the set-point values in the cutting interval and in the coagulation interval. In the cutting interval, a small arc should always be burning so that the indicating device always produces a signal, with the help of which the set-point program can be utilized to continue the cutting action. In the coagulation interval, there should be no burning electric arc. Therefore, there is no signal given by the indicating device to give any reference or setting, and no signal will be given by the indicating device. If the characteristics of the tissue should change, for example through warming up by means of the coagulation process, or through changes in the line voltage of the generator, then there would be no criteria in the indicating means relating to the ignition point of the electric arc as long as the electric arc is not burning.

Figure 5:
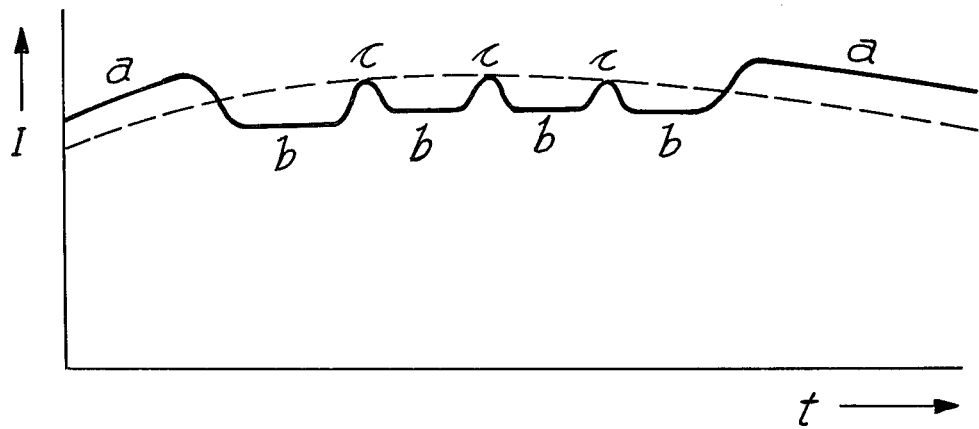
FIG. 5 is a graph showing a mode of operation of one of the embodiments of the invention.

In an advantageous form of this invention, the set-point program is arranged in such a way that, during the coagulation process, the current will be increased periodically in short bursts to locate the ignition point of the electric arc. FIG. 5 shows a typical time sequence for the magnitude of the high frequency current for this purpose. This is the ordinate of the graph. The abscissa is time. The interrupted line shows a typical time dependence of the ignition point of the electric arc in a tissue of varying composition. This broken line shows the current level at and above which an arc will burn, assuming proper voltage. The curves are not horizontal, because it is assumed that the composition of the tissue is changing. The solid line curve shows the real course of current magnitude (I) that is controlled by the set-point program. It shows at segments "*a*" the current in time intervals in which the cutting process occurs. At this time, the current lies above the ignition point of the electric arc and an arc burns. Segments "*b*" are the time intervals during the coagulation process. In these intervals, the current will drop below the ignition point of the electric arc and no arc burns, but current is passed to create heat. However, during these segments, there is no signal from the measuring means. To overcome this deficiency, points "*c*" show moments in time in which the current magnitude (only during coagulation procedure) is periodically increased in short bursts to the ignition point of the electric arc.

The existence of the arc will be evidenced by the generation of the harmonics which will be detected by the measuring means. As soon as the ignition point is reached at the time point "c", and this fact is detected, the current magnitude at the moment will be measured, and its magnitude fed into the set-point program as a new standard. Then it is necessary for the current immediately to be reduced so that the arc is extinguished, because cutting is not desired. The set-point program has been given a suitable order or standard, i.e., the current level at which the arc ignites, and the next coagulation current will be related to it, and be less than the ignition value. The set-point program contains data relating to the difference there should be between the actual current at ignition and the standard, and will therefore reduce the current by some predetermined amount.

During the searching for the ignition point at time points "c", it is important to take into account the fact that the arc will not start immediately after the necessary current level enabling it has been reached. It is, therefore, necessary to allow a little time (e.g., a millisecond) for the arc to start. This fact is related to the rate at which the current itself is to be increased. In a preferred form of this invention, enough time is allowed that the electric arc can occur and be recognized before an excessively large additional increase of current is made. This is done in such a way that the current magnitude at the end of the time interval "b" and up to the ignition point "c" increases gradually. If the increase is too sudden, then the current magnitude would quickly rise above the ignition point, before the electric arc can occur. It is best practice, if one is to find the exact ignition point, to allow the increase of current to occur in small steps and to permit its magnitude to hover at a nearly constant value at every step, and lengthen the duration of each step slightly more than the time that would be needed for ignition of the electric arc. Then the electric arc starts at a current level respective to the exact ignition point.

It is of advantage to build the set-point program and the control process utilizing digital principles, i.e., to increase the current step by step, and to keep the time interval in every step equal to, or equal to a prescribed multiple of, a standard time interval. The set-point programmer 9 will then include a clock which determines the interval duration of the step and/or the interval of the standard time. The magnitude of the steps will be preselected by the sergeon, and is related to the requirements of the operation procedure and the step intervals. In bloodier environments requiring more coagulation, there will be longer coagulation intervals than when tissue is being cut which is not especially laden with blood, or wherein large vessels are expected to be encountered.

The set-point program is produced by a logical circuit and determines if, and in which predetermined time intervals (steps), the current will be changed by an impulse device. Circuits for this purpose are well known, and require no detailed disclosure here. The control means 8 also has an electronic device that sets (in the preset time points "c") the level of the set-point program relative to the measured ignition level of the electric arc.

There are cases in which the bleeding is expected to be very profuse, and in which the tissue will be cooled by the flowing blood. In these cases one needs especially large amounts of heat to close the cut blood vessels. In a favorable form of this invention, a large amount of heat can be brought to the tissue for a very short time. This will be achieved by short impulses of high frequency current during the coagulation interval to a point above the ignition point of the electric arc, but only for such a short duration that cutting itself does not occur. This extreme heat acts only on the surface of the tissue and is restricted to the immediate surroundings of the probe, so that the adverse effects on the albumen are at least localized, and any disadvantage is offset by the promptness of coagulation.

The term "generator" has been utilized herein to describe a source of current at a predetermined frequency, usually a high frequency between about 200KHz–1.7MHz, to produce currents that are acceptable to the human body. These are generally known surgical standards, and such generators are widely known and require no further discussion here. The filters as described herein are conventional types which have band-passes set to pass only the components of interest as described herein. Such filters are completely conventional and require no detailed discussion here. The measuring means may comprise conventional high frequency ammeters or voltmeters, as indicated.

The reference setter 9 is a simple means to determine a predetermined difference between the current at which ignition occurs and the current which should be produced during coagulation. The control means is a simple sequential means operable in response to the input from leads 11 and reference setter 9 to determine the output of the generator in accordance with known techniques.

This invention thereby provides a means for limiting the volume of the electric arc to the minimum extent necessary for the cutting of human tissue, and during coagulation to produce maximum heat without extending into the arc region by periodically referring the system to the point at which an arc is generated.

The means for determining the presence or absence or absence of an arc may be optical, such as an infrared or ultraviolet responsive sensor whose production of an electrical signal would be detected, or, in the preferred embodiment, an all-electrical circuit as already defined.

The term "measuring means" is sometimes used synonymously with "indicating means". Obviously, measuring means 16 and 18, by producing a measurement, will also indicate the existence of an arc. In FIG. 2, the illustrated "indicating means" is simpler, and more generic, and may comprise merely an optical-electrical means responsive to the arc. As such it is less sophisticated that the means shown in FIGS. 3 and 4, which also indirectly measure the volume of the arc. Of course, measuring means can be used also in FIG. 2, and FIGS. 3 and 4 show means for doing it. Of course, if measurements of the arc intensity are made, rather than of harmonics, then appropriate and straight forward circuitry will be supplied for that purpose.

This invention is not to be limited by the embodiments shown in the drawings and described in the description, which are given by way of example and not of limitation, but only in accordance with the scope of the appended claims.

We claim:

1. A method of regulating the current applied to a high-frequency current tissue-cutting device having a thin probe acting as one electrode, a second electrode, and a generator of high-frequency current applying said current to said electrodes, while cutting tissue which tissue has the property of steaming off when heated to high temperature, said method comprising: applying current and voltage of the generator to the electrodes to cause an arc to ignite and burn at the probe, detecting the existence of the arc and measuring its volume, and adjusting the current to the probe to maintain the arc at a predetermined volume.

2. A method according to claim 1 in which the arc is detected optically, and the measurement of its volume is made by optical-to-electrical transducer means.

3. A method according to claim 2 in which the transducer means generates a voltage or a current, and the voltage or the amperage is measured, indirectly to measure the volume of the arc, and to assist in maintaining a predetermined volume.

4. A method according to claim 1 in which the arc is detected by measuring in the circuit to the two electrodes, harmonic components which are caused by the arc when it burns.

5. A method according to claim 4 in which substantially all of the harmonics caused by the arc are summed up and measured.

6. A method according to claim 5 in which the voltage or amperage of the harmonic components is measured, indirectly to measure the volume of the arc, and to assist in maintaining a predetermined volume.

7. A method according to claim 4 in which substantially all of the harmonics except for the third harmonic are filtered out, and the third harmonic is measured.

8. A method according to claim 4 in which the amperage of the harmonic components is measured, indirectly to measure the volume of the arc, and to assist in maintaining a predetermined volume.

9. Apparatus for cutting tissue with the use of a high-frequency electric current, comprising:
a generator of high-frequency electric current;
a thin probe for making a small area contact with tissue to be cut, acting as a first electrode;
a second electrode;
conductive lead means connecting the generator to the electrodes;
indicating means for indicating the existence and volume of an electric arc between the probe and the tissue; and
control means to adjust the current supplied to the probe by the generator to a level to determine and maintain the volume of the arc at a predetermined level.

10. Apparatus according to claim 9 in which the indicating means comprises an optical-electrical transducer responsive to the light of an arc, and productive of an electrical signal respective to it.

11. Apparatus according to claim 9 in which said indicating means is connected to said control means which adjusts the current supplied by the generator.

12. Apparatus according to claim 11 in which a reference setter is connected to the control means for determining the level of the current.

13. Apparatus according to claim 9 in which the indicating means comprises filter means which filters out substantially all wave forms except harmonics generated by the arc, and measuring means which measure the said harmonics and provides a signal to said control means for control of the current supplied by the generator.

14. Apparatus according to claim 13 in which a reference setter is connected to the control means for determining the level of the current.

15. Apparatus according to claim 9 including first filter means for removing harmonics from the generator output, and in which the indicating means comprises measuring means which measure harmonics generated by the arc.

16. Apparatus according to claim 15 in which the measuring means is an ammeter or a voltmeter.

17. Apparatus according to claim 15 in which a reference setter is connected to the control means for determining the level of the current.

* * * * *